(12) United States Patent
Hsu

(10) Patent No.: US 7,896,799 B2
(45) Date of Patent: Mar. 1, 2011

(54) PENIS DEVELOPMENT CORRECTION DEVICE

(76) Inventor: Geng-Long Hsu, Hacienda Heights, CA (US)

( * ) Notice: Subject to any disclaimer, the term of this patent is extended or adjusted under 35 U.S.C. 154(b) by 1067 days.

(21) Appl. No.: 11/627,991

(22) Filed: Jan. 29, 2007

(65) Prior Publication Data

US 2008/0183032 A1    Jul. 31, 2008

(51) Int. Cl.
*A61F 5/00*    (2006.01)
(52) U.S. Cl. ........................................................ 600/39
(58) Field of Classification Search .............. 600/38–41
See application file for complete search history.

(56) References Cited

U.S. PATENT DOCUMENTS 5,667,471 A * 9/1997 Weller et al. .................. 600/39
5,728,043 A * 3/1998 Yong ........................... 600/39
6,793,620 B1 * 9/2004 Droznin et al. ............... 600/39
7,645,228 B2 * 1/2010 Flores .......................... 600/38
2008/0276944 A1 * 11/2008 Cvetanovic .................. 128/845

* cited by examiner

*Primary Examiner*—John P Lacyk
(74) *Attorney, Agent, or Firm*—Alan Kamrath; Kamrath & Associates PA

(57) ABSTRACT

The correction device mainly contains a main tube and a secondary tube for housing the penis, a belt for wearing around a user's waist, and a number of straps connecting the belt to the main and secondary tubes. The main and secondary tubes are attached in parallel together along their axial direction so that the secondary tube provides a buffer space for an erected penis and the penis will not be hurt by the main tube. The straps contains at least an abdomen strap running in front of the user's abdomen, and a perineum strap extending from the belt to run over the buttock and then between the legs of the user to the main tube.

4 Claims, 5 Drawing Sheets

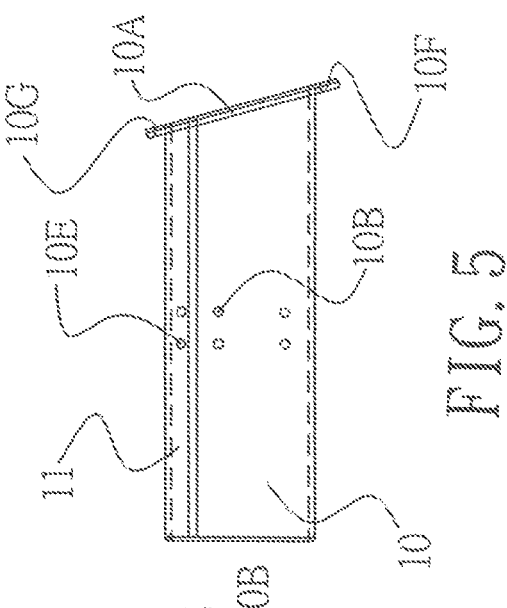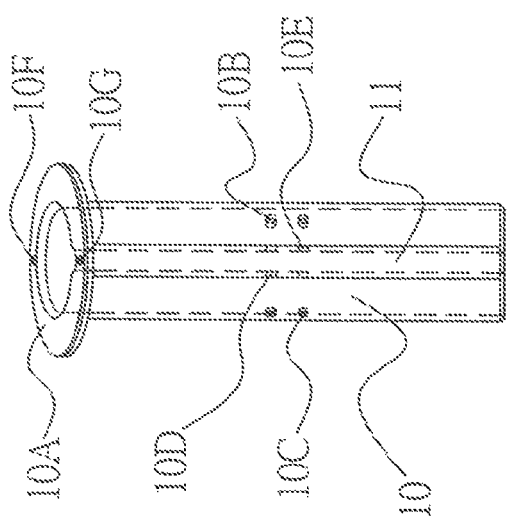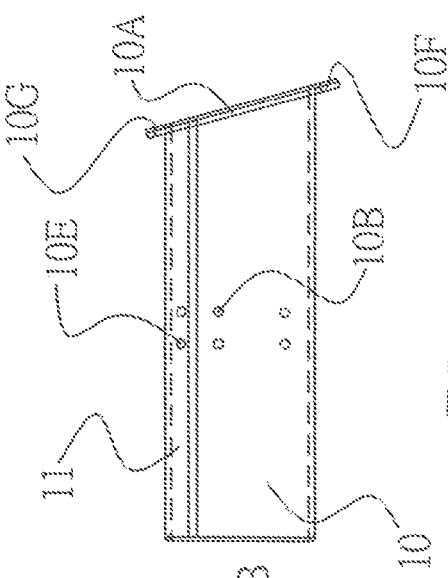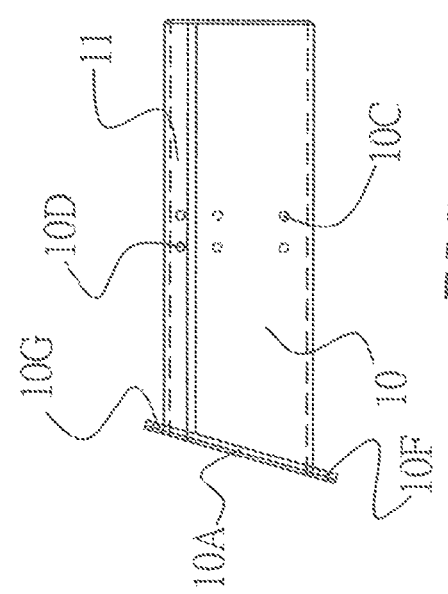

PENIS DEVELOPMENT CORRECTION DEVICE

(a) TECHNICAL FIELD OF THE INVENTION

The present invention generally relates to correction devices and more particularly to a device for helping penis to grow into a straight shape during the organ's development.

(b) DESCRIPTION OF THE PRIOR ART

A lot of young boys have their penises developed into an abnormal skew shape. These young boys are usually ridiculed by their peers, causing some incurable scare on these young minds. These young boys have to carry these scars into their adulthood and live with them for many years to come.

If in an early stage of the penis development such abnormality can be corrected, these young boys then can have a healthier life, both physically and mentally.

SUMMARY OF THE INVENTION

Therefore, a penis development correction device is provided herein. The correction device mainly contains a main tube and a smaller secondary tube for housing the penis, a belt for wearing around a user's waist, and a number of straps connecting the belt to the main and secondary tubes.

The main and secondary tubes are joined side by side together in parallel along their axial direction so that the secondary tube provides a buffer space so that an erected penis will not be hurt by the main tube. The straps contains at least an abdomen strap running in front of the user's abdomen, and a perineum strap extending from the belt to run over the buttock and then between the legs of the user to the main tube.

The foregoing object and summary provide only a brief introduction to the present invention. To fully appreciate these and other objects of the present invention as well as the invention itself, all of which will become apparent to those skilled in the art, the following detailed description of the invention and the claims should be read in conjunction with the accompanying drawings. Throughout the specification and drawings identical reference numerals refer to identical or similar parts.

Many other advantages and features of the present invention will become manifest to those versed in the art upon making reference to the detailed description and the accompanying sheets of drawings in which a preferred structural embodiment incorporating the principles of the present invention is shown by way of illustrative example.

BRIEF DESCRIPTION OF THE DRAWINGS

FIG. 3 is a top view of the main and secondary tubes of the penis development correction device of FIG. 1.

FIG. 4 is a front view of the main and secondary tubes of the penis development correction device of FIG. 1.

FIG. 5 is a left side view of the main and secondary tubes of the penis development correction device of FIG. 1.

FIG. 6 is a right side view of the main and secondary tubes of the penis development correction device of FIG. 1.

DETAILED DESCRIPTION OF THE PREFERRED EMBODIMENTS

The following descriptions are exemplary embodiments only, and are not intended to limit the scope, applicability or configuration of the invention in any way. Rather, the following description provides a convenient illustration for implementing exemplary embodiments of the invention. Various changes to the described embodiments may be made in the function and arrangement of the elements described without departing from the scope of the invention as set forth in the appended claims.

Figure 1:
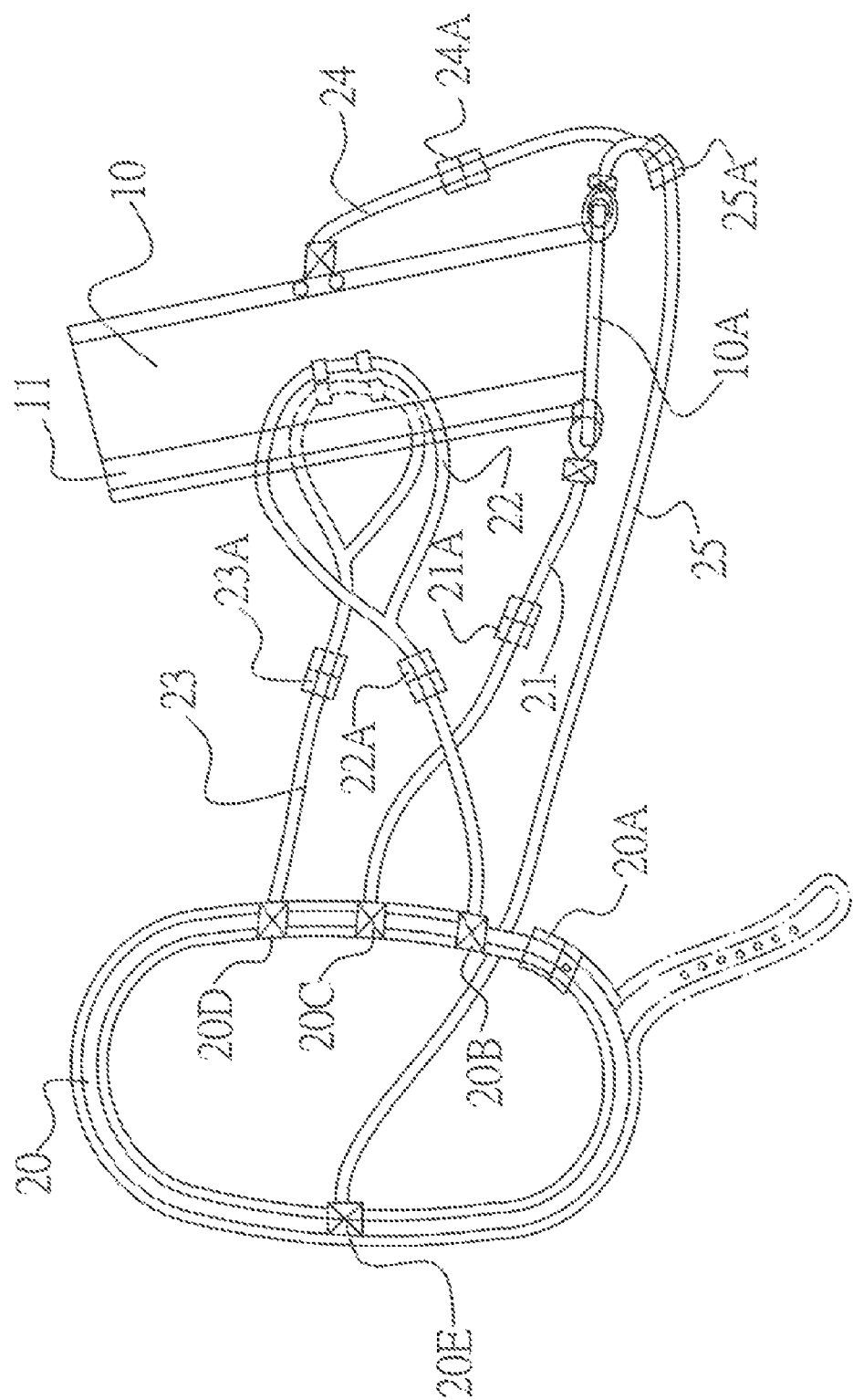
FIG. 1 is a schematic diagram showing the various components of a penis development correction device according to an embodiment of the present invention.
Figure 2:
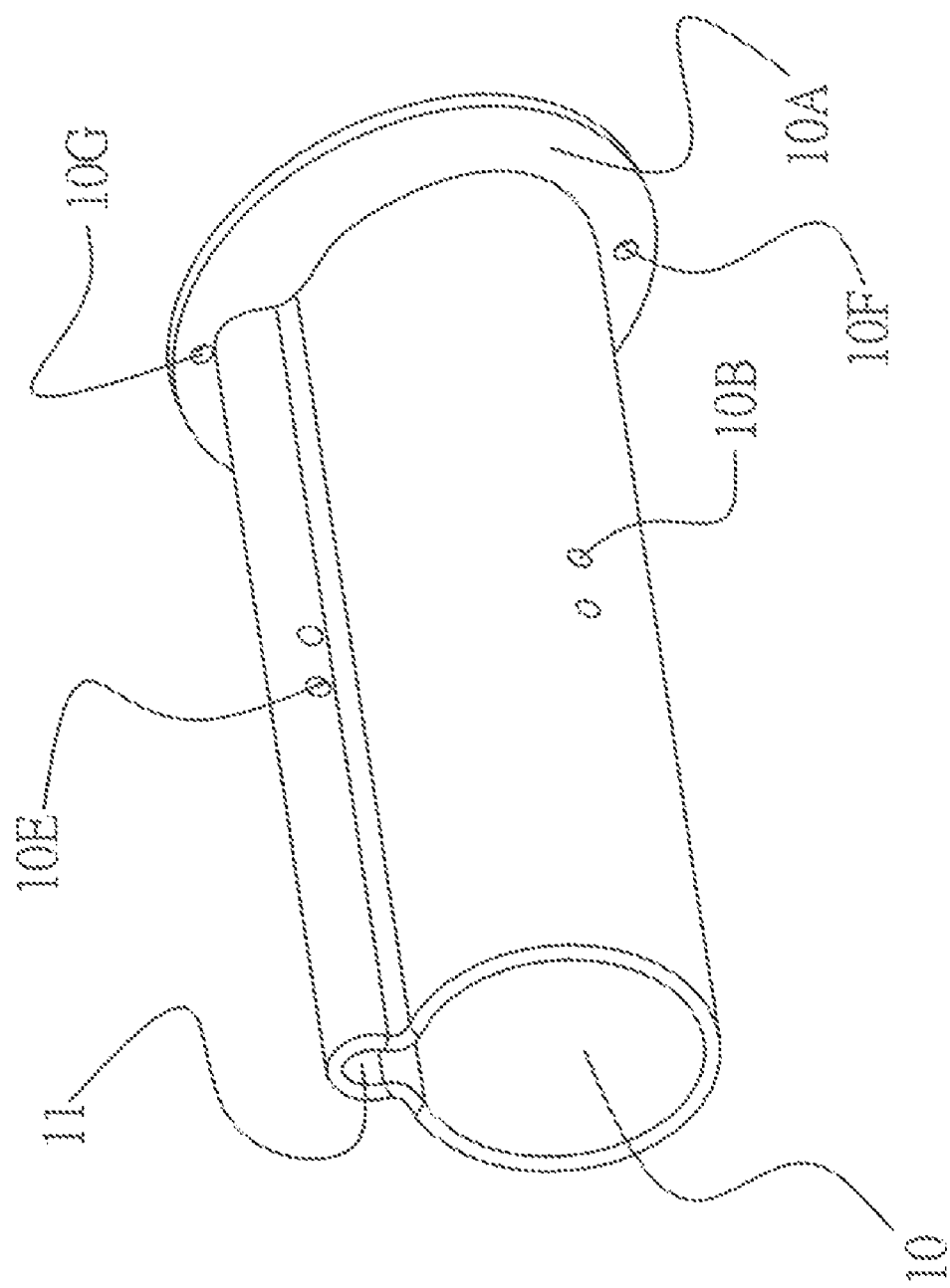
FIG. 2 is a perspective view of the main and secondary tubes of the penis development correction device of FIG. 1.

As illustrated in FIGS. 1 to 6, the correction device contains a main tube 10 made by silica gel into a transparent tubular shape having 150 mm in length, 35 mm in diameter, and 2 mm in thickness. The correction device also contains a smaller secondary tube 11, also made by silica gel into a transparent tubular shape having 141 mm in length, 7 mm in diameter, and 2 mm in thickness. The walls of the main and secondary tubes 10 and 11 have a slot opening running end to end in the axial direction, respectively. The main and secondary tubes 10 and 11 are joined together so that their slot openings coincide with each other and the internal spaces within the main and secondary tubes 10 and 11 are connected. The main tube 10 is for housing the penis to be corrected and, by the confinement of the main tube 10, the penis will develop into a straight normal shape. The secondary tube 11 is configured so that it is on the top side of the main tube 10 (therefore, on the front side of the penis housed inside the main tube 10 where the penis tissue is the hardest and the least sensitive). When the penis erects, due to the flexibility of the silica gel and the buffering space provided by the secondary tube 11, the main tube 10 will not cause pain or damage to the erected penis. The main and secondary tubes 10 and 11 can be integrally molded into the shape shown in the drawings. Please note that, at the roots (i.e., the back ends) of the main and secondary tubes 10 and 11, a flange 10A is provided.

The correction device further contains a belt 20 made by leather into having 1030 mm in length, 30 mm in width, and 2 mm in thickness. The belt 20 has a buckle 20A for adjusting the length when the belt 20 is worn around the waist of a user.

The correction device further contains a number of straps whose two ends are connected to the belt 20 and the main and secondary tubes 10 and 11, respectively. An abdomen strap 21 has its one end connected to a connector element 20C at an appropriate location along the belt 20. The abdomen strap 21 has the other end connected to a through hole 10G on the flange 10A above the secondary tube 11. As such, the abdomen strap 21 will run substantially vertically in front of the user's abdomen. Along the length of the abdomen strap 21, an adjustment element 21A is provided at an appropriate location so that the length of the abdomen strap 21 can be adjusted to fit a specific user. A perineum strap 25 has its one end connected to a connector element 20E at an appropriate location along the belt 20. The perineum strap 25 has the other end connected to a through hole 10F on the flange 10A beneath the main tube 10. As such, the perineum strap 25 will extend from the belt 20 to run over the buttock and then between the legs of the user to the flange 10A. Along the length of the perineum strap 25, an adjustment element 25A is provided at an appropriate location so that the length of the perineum strap 25 can be adjusted to fit a specific user.

Along the walls of the main and secondary tubes 10 and 11, a number of pairs of through holes 10B, 10C, 10D, and 10E are provided for the connection of three additional safety straps 22, 23, and 24. The first and second safety straps 22 and 23 have their one ends connected to two connector elements 20B and 20D at the two sides of the connector element 20C, respectively, along the belt 20. The first and second safety straps 22 and 23 then have the other ends connected to two pairs of the through holes 10B, 10D, and 10E, respectively. On the other hand, from an appropriate location of the perineum strap 25, the third safety strap 24 is branched to connect to the pair of through holes 10C. Along the lengths of the safety straps 22, 23, and 24, adjustment elements 22A, 23A, and 24A are provided at appropriate locations so that the lengths of the safety straps 22, 23, and 24 can be adjusted to fit a specific user, respectively.

Figure 7:
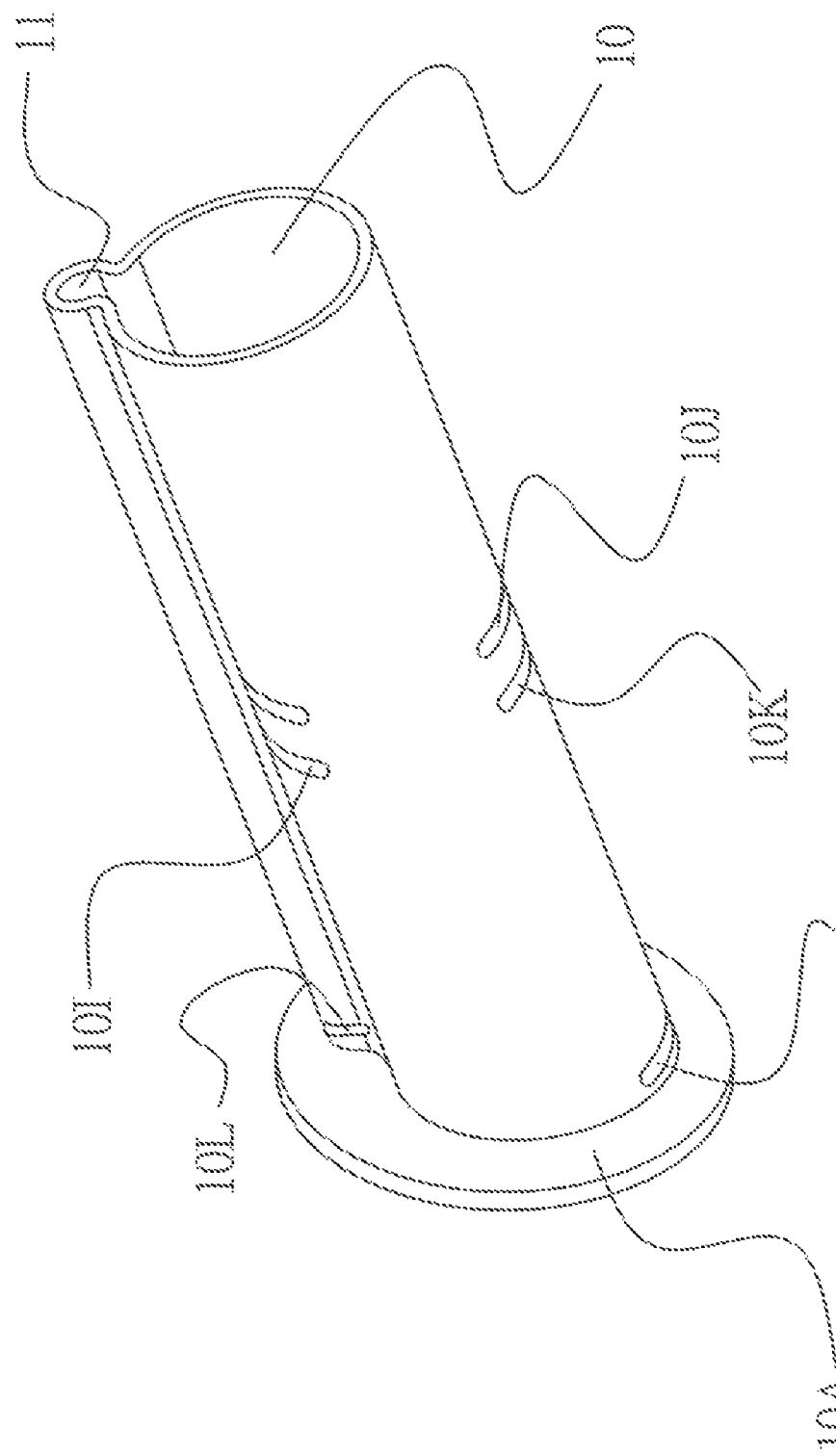
FIG. 7 is a perspective view of the main and secondary tubes of another embodiment of the penis development correction device.
Figure 8:
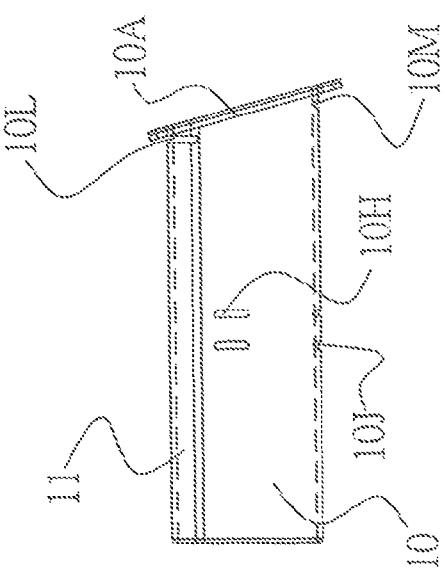
FIG. 8 is a top view of the main and secondary tubes of the penis development correction device of FIG. 7.
Figure 9:
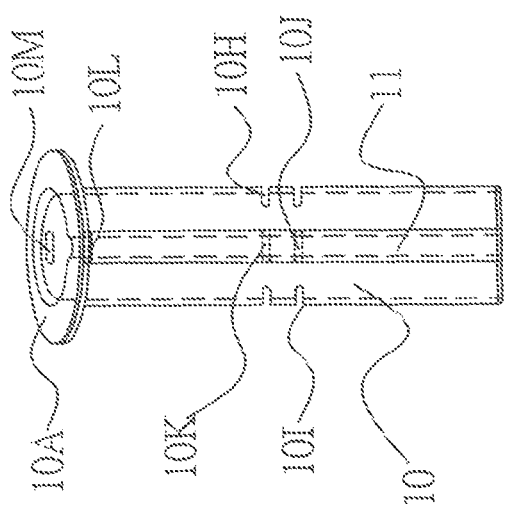
FIG. 9 is a front view of the main and secondary tubes of the penis development correction device of FIG. 7.
Figure 10:
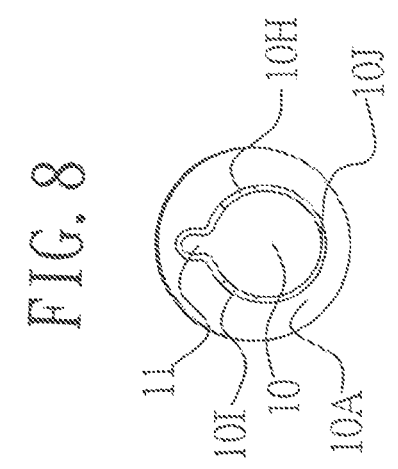
FIG. 10 is a left side view of the main and secondary tubes of the penis development correction device of FIG. 7.
Figure 11:
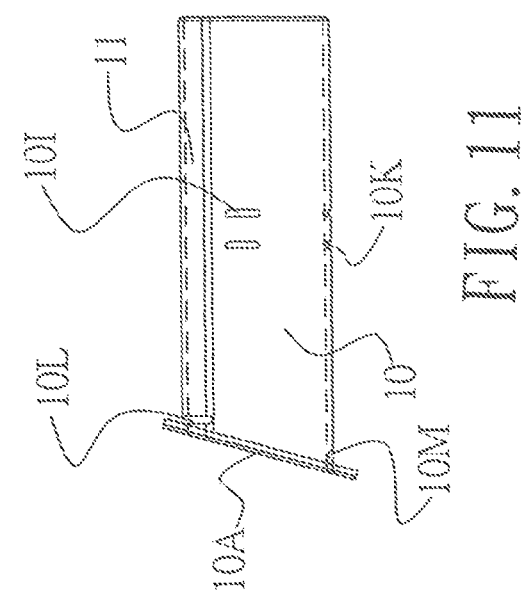
FIG. 11 is a right side view of the main and secondary tubes of the penis development correction device of FIG. 7.

FIGS. 7~11 show another embodiment of the main and secondary tubes 10 and 11. As illustrated, this embodiment provides through slots 10L and 10M on the walls near the roots of the main and secondary tubes 10 and 11 for the connection of the abdomen and perineum straps 21 and 25, respectively. Then, instead of having pairs of through holes, this embodiment provides pairs of through slots 10H, 10I, 10J, and 10K on the wall of the main tube 10 for the connection of the various safety straps 22, 23, and 24, respectively.

It will be understood that each of the elements described above, or two or more together may also find a useful application in other types of methods differing from the type described above.

While certain novel features of this invention have been shown and described and are pointed out in the annexed claim, it is not intended to be limited to the details above, since it will be understood that various omissions, modifications, substitutions and changes in the forms and details of the device illustrated and in its operation can be made by those skilled in the art without departing in any way from the spirit of the present invention.

I claim:

1. A penis development correction device comprising:
   a main tube adapted for housing the penis of a user;
   a secondary tube having a diameter smaller than that of said main tube, said secondary tube attached in parallel to a top side of said main tube with an end-to-end slot opening therebetween, a flange being provided at roots of said main and secondary tubes;
   a belt adapted for wrapping around the waist of said user;
   an abdomen strap adapted for running in front of the abdomen of said user, said abdomen strap connecting said belt to said flange;
   a perineum strap adapted for running over the buttock and between the legs of said user, said perineum strap connecting said belt to said flange;
   a plurality of safety straps connecting said belt to said main tube or said secondary tube, respectively; and
   an additional safety strap connecting said perineum strap to said main tube.

2. The penis development correction device according to claim 1, wherein at least one of said belt, said abdomen strap, said perineum strap, and said safety straps has an adjustment element along the length for adjusting the length of said belt or strap.

3. The penis development correction device according to claim 1, wherein a plurality of pairs of through holes are provided on the walls of said main and secondary tubes for the connection of said safety straps, respectively.

4. The penis development correction device according to claim 1, wherein a plurality of pairs of through slots are provided on the walls of said main and secondary tubes for the connection of said safety straps, respectively.

* * * * *